United States Patent [19]

Oeda et al.

[11] Patent Number: 5,231,008

[45] Date of Patent: Jul. 27, 1993

[54] PRODUCTION OF INSECTICIDAL PROTEIN OF BACILLUS THURINGIENSIS SUBSP. AIZAWAI IPL BY THE EXPRESSION OF INSECTICIDAL PROTEIN GENE IN HOST CELLS

[75] Inventors: Kenji Oeda, Osaka; Kazuyuki Oshie, Hyogo; Masatoshi Shimizu, Hyogo; Keiko Nakamura, Hyogo; Hideo Ohkawa, Hyogo, all of Japan

[73] Assignee: Sumitomo Chemical Company, Limited, Osaka, Japan

[21] Appl. No.: 715,741

[22] Filed: Jun. 18, 1991

Related U.S. Application Data

[63] Continuation of Ser. No. 611,475, Nov. 9, 1990, abandoned, which is a continuation of Ser. No. 449,353, Dec. 13, 1989, abandoned, which is a continuation of Ser. No. 920,791, Oct. 20, 1986, abandoned.

[30] Foreign Application Priority Data

Oct. 28, 1985 [JP] Japan ................. 60-242528
Feb. 6, 1986 [JP] Japan ................. 61-24563
Feb. 25, 1986 [JP] Japan ................. 61-40925

[51] Int. Cl.$^5$ .............. C12P 21/00; C12N 15/00; C12N 15/11; C12N 15/70
[52] U.S. Cl. ................. 435/69.1; 435/258.3; 435/252.33; 435/320.1; 530/23.71; 935/11
[58] Field of Search ............... 435/69.1, 71.2, 91, 435/172.1, 172.3, 252.3–252.35, 320.1; 536/27, 23.71; 935/11, 29, 72, 73, 74

[56] References Cited

U.S. PATENT DOCUMENTS

| | | | |
|---|---|---|---|
| 4,467,036 | 8/1984 | Schnepf et al. | 435/68 |
| 4,695,455 | 9/1987 | Barnes et al. | 435/68 |
| 4,918,006 | 4/1990 | Ellar et al. | 435/69.1 |

FOREIGN PATENT DOCUMENTS

| | | | |
|---|---|---|---|
| 0063949 | 3/1982 | European Pat. Off. | 435/172.3 |
| 0093062 | 2/1983 | European Pat. Off. | 435/172.3 |
| 0153166 | 8/1985 | European Pat. Off. | 435/172.3 |
| 0186379 | 7/1986 | European Pat. Off. | 435/172.3 |
| 8601536 | 3/1986 | World Int. Prop. O. | 435/172.3 |

OTHER PUBLICATIONS

Klier et al.; in Mol. Biol. Microb. Differ., Proc. Int. Spore Conf., 9th 1984, 1985, Hoch et al. (ed.), Am. Soc. Microbiol., Washington, D.C., pp. 217–224.
Klier et al.; Embo J. 1: 791 (1982).
Schnepf et al., J. Biol. Chem., 260, No. 10, pp. 6264–6272 (1985).
Schnepf et al., J. Biol. Chem., 260, No. 10, pp. 6273–6280 (1985).
Shibano et al., Gene, 34, pp. 243–251 (1985).
Adang et al., Gene, 36, pp. 289–300 (1985).
Shivakumar et al., J. Bact., vol. 166, No. 3, pp. 194–204 (1986).
Thorne et al., J. Bact., vol. 166, No. 3, pp. 801–811 (1986).
Wabiko et al., DNA, vol. 5, No. 4, pp. 305–314 (1986).
Aronson et al., Microbiological Reviews, vol. 50, No. 1, pp. 1–24 (1986).
Klier et al., Chem. Abstracts, vol. 103, p. 214 (1985) 15223u.
Jarrett, Chem. Abstracts, vol. 103, p. 355 (1985) 67996t.

*Primary Examiner*—James Martinell
*Attorney, Agent, or Firm*—Birch, Stewart, Kolasch & Birch

[57] ABSTRACT

Insecticidal protein of *B. thuringiensis* subsp. aizawai IPL is produced by growing a transformant microorganism harboring a recombinant expression vector carrying a gene coding for the insecticidal protein.

15 Claims, 6 Drawing Sheets

```
                                                                                        TGTTAACACCCTGGGTCAAAAATTGATATTTAGTAA
AATTAGTTGCACTTGTCGCATTTTTCATAAGATGAGTCATATGTTTAAATTGTAGTAATGAAAAACAGTATTATCATAATGAATTGTATCTTAATAAAAGAGATGGAGGTAACTT
         10        20        30        40        50        60        70        80        90       100       110       120
ATGGATAACAATCCGAACATCAATGAATTCCTTATAATTGTTAGTAACCCTGAAGTAGAAGTATTAGGTGGAGAAAGAATAGAAACTGGTTACACCCCAATCGATATTTCCTTG
MetAspAsnAsnProAsnIleAsnGluCysIleProTyrAsnCysLeuSerAsnProGluValGluValLeuGlyGlyGluArgIleGluThrGlyTyrThrProIleAspIleSerLeu
        130       140       150       160       170       180       190       200       210       220       230       240
TCGCTAACGCAATTCTTTTGAGTGAATTTGTTCCCGGTCTGATTGTGTTAGGACTAGTTGATATAATATGGGAATTTGGTCCCCTCAATGGACGCATTTCTTGTACAAATT
SerLeuThrGlnPheLeuLeuSerGluPheValProGlyAlaGlyPheValLeuValAspIleIleTrpGlyIleProSerGlnTrpAspAlaPheLeuValGlnIle
        250       260       270       280       290       300       310       320       330       340       350       360
GAACAGTTAATTAACCAAGAATAGAAGAATTCGCTAGGAACCAGCCATTCTAGATTAGAAGGACTAAGCAATCTTATCAAATTACCAGAGAATCTTTTAGAGAGTGGGAAGCAGAT
GluGlnLeuIleIleAsnGlnAsnArgIleGluGluPheAlaArgAsnGlnAlaIleSerArgLeuGluGlyLeuSerAsnLeuTyrGlnIleLeuTyrAlaGluSerPheArgGluValAlaAsp
        370       380       390       400       410       420       430       440       450       460       470       480
CCTACTAATCCAGCATTAAGACAGAGATGCGTATTCAATTCAATTGACACAGTGCCCTTACAACCGCTATTCCTCTTTTGCAGTTCAAAAATTATCAAGTTCCTCTTTTATCAGTA
ProThrAsnProAlaLeuArgGluArgMetArgIleGlnPheAlaValGlnAsnSerAlaLeuThrThrAlaIleProLeuPheAlaValGlnAsnTyrGlnValProLeuLeuSerVal
        490       500       510       520       530       540       550       560       570       580       590       600
TATGTTCAAGCTGCAAATTTACATTTATCAGTTTGAGAGATGTTTCAGTGTTGGACAAAGGTGGGGATTTGATGCCGACTATCAATAGTCGTTATAATGATTAACTAGGCTTATT
TyrValGlnAlaAlaAsnLeuHisLeuSerValLeuArgAspValSerValPheGlyLeuArgTrpGlyLeuAsnArgTyrAsnAspLeuThrArgLeuIle
        610       620       630       640       650       660       670       680       690       700       710       720
GGCAACTATACAGATCATGCTGTACGCTGGTACAATACGGATTAGAGCCGGTATGGGACCGGATTCTAGAATGGATAAGATAATCAATTAGAAGAGAATTAACACTAACTGTA
GlyAsnTyrThrAspHisAlaValArgTrpTyrAsnThrGlyLeuArgValTrpGlyValProAspSerArgAspTyrProIleArgTyrAsnGlnPheArgArgGluLeuThrLeuThrVal
        730       740       750       760       770       780       790       800       810       820       830       840
TTAGATATCGTTCTTCCTATTCCGAACTATGATAGTAGAACGTATCCAATTCGAACAGTTTCCAATTAACAGAAATTTATACAACCCAGTATTAGAAAATTTGATGGTAGTTTT
LeuAspIleValSerLeuPheProAsnTyrAspSerArgThrTyrProIleArgThrValSerGlnLeuPheArgLeuIleTyrThrAsnProValLeuGluAsnPheAsnGlySerPhe
        850       860       870       880       890       900       910       920       930       940       950       960
CGTGCTCTGGCTCAGGGCATAGAAGGAGTATTAGAGCTCCACATTGATGAGTCCACATTCTAACAGTATACTTAACAGTATATAACCATCTATACGATGCTCATAGAGGAGAATATTATTGGTCAGGGCATCAA
ArgAlaLeuAlaGlnGlyIleGluGlyValLeuGluSerProHisLeuMetAspIleArgSerProHisLeuMetAspIleArgSerProIleLeuAsnSerIleThrIleTyrThrAspAlaHisArgGlyGluTyrTyrTrpSerGlyHisGln
        970       980       990      1000      1010      1020      1030      1040      1050      1060      1070      1080
ATAATGGCTTCTCCTGTAGGGTTTCGGGGCCAGAATTCACTTTCGCTATATGGAAATGCAGCTCCACAACAACGTATTGTTGCTCAACTAGGTCAGGGCGTGTATAGA
IleMetAlaSerProValGlyPheSerGlyProValPheSerGlyProGluPheThrPheProLeuTyrGlyPheMetGlyAsnAlaAlaProGlnIleArgIleValAlaAlaProGlnIleLeuGlyLeuValTyrArg
       1090      1100      1110      1120      1130      1140      1150      1160      1170      1180      1190      1200
ACATTATCGTCCACTTATATAGAAGACCTTTAATATAGGATAAATAATCAACAACTATCTGTTCTTGACGGGACAGAATTTGCTTATGGAACCTCCTCAAATTGCCATCCGCTGTA
ThrLeuSerThrLeuTyrArgArgProPheAsnIleGlyIleAsnAsnGlnLeuGlnLeuSerValLeuAspGlyThrGluPheAlaTyrGlyThrSerSerAsnLeuProSerAlaVal
```

FIG. 2(2)

```
         1210      1220      1230      1240      1250      1260      1270      1280      1290      1300      1310      1320
TACAGAAAAGCGGAACGGTAGATTCGCTGATGAATAAACTACCGCCACTGCCAAGATTAGTCATGATTAAGCCATGTTTCATGTTTCGTTCAGGCTTT
TyrArgLysSerGlyThrValAspSerLeuAspGluIleProProGlnAsnAsnValProProArgGlnGlyPheSerHisArgLeuSerHisValSerMetPheArgSerGlyPhe 1330      1340      1350      1360      1370      1380      1390      1400      1410      1420      1430      1440
AGTAATAGTAGTGTAAGTATAATAAGAGCTCCTATGTTCTCTTGGATACATCGTAGTGCTGAATTTAATAATATAATTCCTTCATCACAAATTACACAAATACCTTAACAAATCTACT
SerAsnSerSerValSerIleIleArgAlaProMetPheSerTrpIleHisArgSerAlaGluPheAsnAsnIleIleProSerSerGlnIleThrGlnIleProLeuThrLysSerThr 1450      1460      1470      1480      1490      1500      1510      1520      1530      1540      1550      1560
AATCTTGGCTCTCTGGAACTTCTGTCGTTAAAGGACCAGATTTACAGGAGGAGATATTCTTGAAGAACTTCACCTGGCCAGATTCAACTTAAGAGTAAGACTTAAGAGTAAATATTACTGCACCATTATCA
AsnLeuGlySerGlyThrSerValValLysGlyThrArgArgArgTyrPheThrGlyLysAspIleLeuArgArgThrSerProGlyGlnIleSerThrLeuArgValAsnIleThrAlaProLeuSer 1570      1580      1590      1600      1610      1620      1630      1640      1650      1660      1670      1680
CAAAGATATCGGGTAAGAATTCGCTACGCTTCTACCACAAATTACAATTCCATACATCAATTGACGGAAGACCTATTAATCAGGGAATTTTCAGCAACTATGAGTAGTGGGAGTAAT
GlnArgTyrArgValArgIleArgTyrAlaSerThrThrAsnLeuGlnPheHisThrSerIleAspGlyArgProIleAsnGlnGlyAsnPheSerAlaThrMetSerSerGlySerAsn 1690      1700      1710      1720      1730      1740      1750      1760      1770      1780      1790      1800
TTACAGTCCGAAGCTTAGGACTGTAGTTTACTACTCCGTTTAACTTTCAAATGGATCAAGTGTATTTACGTTAAGTGCTCATGTCTCAATTCAGGCAATGAAGTTTATATAGAT
LeuGlnSerGlySerPheArgThrValProAlaGluValProPheTyrTyrAsnPheAsnPheSerSerAsnGlySerSerValPheThrLeuSerAlaHisValPheAsnSerGlyAsnValTyrIleAsp 1810      1820      1830      1840      1850      1860      1870      1880      1890      1900      1910      1920
CGAATTGAATTTGTTCCGGCAGAAGTAACCTTTGAGGCAGAATATGATTAGAAAGAGCACAAAAGGCGGTGAATGAGCTGTTTACTTCTTCCAATCAAATCGGGTTAAAACAGATGTG
ArgIleGluPheValProAlaGluValProPheGluAlaGluTyrAspLeuArgAlaLysGlnLysAlaValAsnGluLeuPheThrSerSerAsnGlnIleGlyLeuLysThrAspVal 1930      1940      1950      1960      1970      1980      1990      2000      2010      2020      2030      2040
ACGGATTATCATATTGATCAAGTCATCCAATTAGTTGAGTGTTATCTGATGAATTTGTCTGATGAATTTGTCTGATGAATTGTCCGAGAAGTCAAACATGCGAAGCGACTAGTGATGAG
ThrAspTyrHisIleAspGlnValIleGlnLeuValGluCysTyrLeuSerAspGluAspPheCysLeuAspLeuSerAspGluLysSerGluLysValLysHisAlaLysArgLeuSerAspGlu 2050      2060      2070      2080      2090      2100      2110      2120      2130      2140      2150      2160
CGGAATTTACTTCAAGATCCAAACTTTAGAGGGATCAATAGACAACTTAGAGGAGGAAGTACGGATATTACCATCCAAGGAGGCGATGACGTATTCAAAGAGAATTACGTT
ArgAsnLeuLeuGlnAspProAsnPheArgGlyIleAsnAspArgGlnLeuAspArgGlyTrpArgGlySerThrAspIleThrIleGlyLysAspAlaAspValPheLysGluAsnTyrVal 2170      2180      2190      2200      2210      2220      2230      2240      2250      2260      2270      2280
ACGCTATTGGGTACCTTTGATGAGTGCTATCCAACGTATTATTCAACAAAATAGAGTCGAAATTAAAAGCCTTACCAATTAAGAGGTATATCGAAGATAGTCAAGAC
ThrLeuLeuGlyThrPheAspGluCysTyrProThrTyrLeuTyrGlnLysIleAspLysLeuLysAlaTyrThrArgTyrGlnLeuArgGlyTyrIleGluAspSerGlnAsp 2290      2300      2310      2320      2330      2340      2350      2360      2370      2380      2390      2400
TTAGAAATCTATTAATTCGCTACAATGCCAAACACGAAACAGTAAATGTGCCAGTTACGGGTTCCTATGCCGCTTCAGCCCCAAGTCAATCGGAAAATGTGCCAATCATCCCAT
LeuGluIleTyrLeuIleArgTyrAsnAlaLysHisGluThrValAsnValProGlyThrGlyLeuSerLeuTrpProLeuSerAlaProSerProIleGlyLysCysAlaHisHisSerHis
```

PRODUCTION OF INSECTICIDAL PROTEIN OF BACILLUS THURINGIENSIS SUBSP. AIZAWAI IPL BY THE EXPRESSION OF INSECTICIDAL PROTEIN GENE IN HOST CELLS

This application is a continuation of application Ser. No. 07/611,475 filed on Nov. 9, 1990, now abandoned which is a continuation of Ser. No. 07/449,353 filed Dec. 13, 1989, now abandoned, which is a continuation of Ser. No. 06/920,791 now abandoned.

BACKGROUND OF THE INVENTION

The present invention relates to the production of an insecticidal protein of *Bacillus thuringiensis* subsp. aizawai IPL by the DNA recombinant technology. More particularly, it relates to a gene coding for the insecticidal protein of *Bacillus thuringiensis* subsp. aizawai IPL, which has a potent insecticidal activity against noxious insects belonging to the order, Lepidoptera, such as larvae of diamond-back moth (*Plutella maculipennis*) and cotton cutworm (*Spodoptera litura*), and to an expression plasmid carrying the said gene and being capable of expressing the insecticidal protein in host cells. It also relates to a transformant microorganism harboring the said expression plasmid and being capable of producing the insecticidal protein, and to a process for producing the insecticidal protein comprising culturing the said transformant microorganism in a suitable medium.

It has been known that microorganisms classified as *Bacillus thuringiensis* produce 1–2 μm in length of crystals of insecticidal protein in their sporulation phase, and that the insects that have eaten the protein stop eating and die from rupture of their intestines. Microorganisms belonging to *Bacillus thuringiensis* are further classified into 29 subspecies according to the flagella antigen, the esterase pattern and the like, and each of them exhibits a distinct and particular insecticidal activity.

SUMMARY OF THE INVENTION

The present inventors have studied aiming at the utilization, as insecticidal agents, of the insecticidal protein of *Bacillus thuringiensis* subsp. aizawai IPL, which exhibits a potent insecticidal activity against noxious insects belonging to the order, Lepidoptera, in particular, larvae of diamond-back moth and cotton cutworm which are harmful to vegetable crops, and, as a result, have completed the present invention.

Specifically, the inventors have succeeded in cloning of a gene coding for the insecticidal protein of *Bacillus thuringiensis* subsp. aizawai IPL having a strong insecticidal activity against larvae of diamondback moth and cotton cutworm, and elucidated the entire DNA sequence of 3465 base pairs (bp) of the structural gene coding for the insecticidal protein, as well as the primary structure of the insecticidal protein. The inventors have also constructed expression plasmids by inserting the said gene into various expression vectors and created transformant microorganisms by transforming microorganisms with each of the said expression plasmids.

BRIEF DESCRIPTION OF THE DRAWINGS

In the accompanying drawings

FIG. 2 (1)–(3) shows the entire DNA sequence of the insecticidal protein gene consisting of 3465 base pairs. The upper lines indicate the DNA sequence and the lower the deduced amino acid sequence. The region from the base No. 1 through No. 3465 is the structural gene coding for the insecticidal protein.

DETAILED DESCRIPTION OF THE INVENTION

The inventors have provided a method for producing the insecticidal protein of *Bacillus thuringiensis* subsp. aizawai IPL in a large scale, which method is characterized by culturing such a transformant microorganism. The insecticidal protein gene of *Bacillus thuringiensis* subsp. aizawai IPL can be identified by the DNA sequence given in FIG. 2, or its deduced amino acid sequence given in FIG. 2.

A plasmid containing the insecticidal protein gene of the present invention can be obtained by first preparing a gene library from the plasmid DNA of *Bacillus thuringiensis* subsp. aizawai IPL and then screening the library with a suitable probe, for example, a synthetic oligonucleotide designed based on the DNA sequence given in FIG. 2, or the DNA sequence of an insecticidal protein gene of *Bacillus thuringiensis* HD-1 Dipel, which is known to closely relates to *Bacillus thuringiensis* subsp. aizawai IPL, for the isolation of the plasmid containing the insecticidal protein gene of the present invention.

In preparing the recombinant plasmid carrying the insecticidal protein gene of the present invention, it is preferable to select a clone of *B. thuringiensis* subsp. aizawai IPL exhibiting a strong insecticidal activity as a source of the gene.

As is well known, with respect to various amino acids, the DNA sequence coding for a particular amino acid is not limited to a single codon, but there are plural acid sequence for one amino acid. Likewise, the DNA sequence coding for the amino acid sequence of the insecticidal protein of *B. thuringiensis* subsp. aizawai IPL is not limited only to the naturally occurring one but there are many possible DNA sequences coding for the insecticidal protein. It should be understood that the present invention includes not only the natural DNA sequence coding for the insecticidal protein of *B. thuringiensis* subsp. aizawai IPL elucidated by the present invention as given in FIG. 2, but also other DNA sequences which code for the amino acid sequences of the insecticidal protein of *B. thuringiensis* subsp. aizawai IPL elucidated by the present inventors.

Moreover, it is known that it is possible to artificially introduce some changes in the DNA sequence in a given gene without altering the substantial properties to be expressed by the gene, or rather with an improvement of such properties. In the case of the insecticidal protein gene of the present invention, which, as mentioned above, may be of the naturally occurring sequence or artificial ones, it is possible to artificially introduce some additions, deletions or substitutions in the DNA sequence to create equivalent or improved insecticidal protein genes. It should be understood that the present invention emcompasses the naturally occurring sequence, as well as such modified sequences.

The expression vector plasmids which enable microorganisms, such as *E. coli*, to produce the insecticidal protein of *B. thuringiensis* subsp. aizawai IPL in the cells can be constructed by inserting the gene coding for the insecticidal protein of *B. thuringiensis* subsp. aizawai IPL into a suitable expression vector such as pUC18 containing lac promoter (Pharmacia), pKK223-4 containing tac promoter of *E. coli*, as well as the terminator of rrbB ribosome RNA, pDR720 having trp promoter (Pharmacia), and an inducible expression vector pPL-Lambda (Pharmacia).

By the transformation of host cells such as *E. coli*, e.g., *E. coli* JM103 strain (Pharmacia), with each of the expression vector plasmids obtained as above, the transformant cells which produce the insecticidal protein in the cells are prepared. The thus prepared transformant cells are grown in a suitable medium under suitable conditions to produce the insecticidal protein in large scale. This process can advantageously be performed by adding an inducer, isopropylthiogalactoside in the culture medium at an early stage of the cultivation.

After the cultivation, the produced insecticidal protein can easily be recovered as condensed aggregates by, for example, ultrasonification of the cells, followed by centrifugation.

For the production of the insecticidal protein, not only the *E. coli*-vector system, but also any of other microorganism-vector systems, such as *Bacillus subtilis*, *Saccharomyces cerevisiae*, Pseudomonas and Actinomycetes-vector systems may also be used taking the advantage of each of the host-vector systems.

The following examples are given to illustrate the invention more precisely. These examples are not intended to limit the present invention in any way. It is to be understood that the invention includes any modifications or improvements thereof.

Isolation of the insecticidal protein gene

Selection of *B. thuringiensis* subsp. aizawai IPL No. 7 having a potent insecticidal activity against insects belonging to the order, Lepidoptera, such as larvae of diamond-back moth and cotton cutworm.

Step 1

Purification of *B. thuringiensis* subsp. aizawai IPL

*B thuringiensis* subsp. aizawai IPL (maintained at the U. S. Department of Agriculture Research Service) was grown on a PY plate culture medium [tryptone (Difco) 10 g/l, NaCl (Nakarai Chemical) 5 g/l, yeast extract (Difco) 5 g/l, agar (Difco) 12 g/l] to give 32 clones in pure culture. The plasmid analysis of the clones was conducted as follows: Each clone was grown in 10 ml of a PY liquid medium (the same composition as that of the PY plate culture medium except that no agar was used) for 24 hours and the cells were harvested by centrifugation (8,000×g, 10 minutes). A plasmid DNA was isolated from the cells according to the method of Birnboim and Doly [Nucleic Acid Res. 7, 1513–1523 (1979)] and analyzed by 0.4% agarose gel electrophoresis to find that no single common plasmid pattern was observed with respect to the 32 clones, and that they are divided into at least 9 groups according to their plasmid patterns.

The clone with which 12 plasmid DNA bands of 4.0 Md, 4.8 Md, 5.4 Md, 8.5 Md, 12 Md, 15 Md, 17 Md, 21 Md, 37 Md, 40 Md, 50 Md, and 52 Md were observed was named as *Bacillus thuringiensis* subsp. aizawai IPL No. 7, and deposited at the Fermentation Research Institute, 1-3, Higashi 1 chome, Yatabe-machi Tsukuba-gun Ibaraki-ken 305, Japan, on Feb. 18, 1986, under the deposition No. FERM P-8654, and also under the deposition NO. FERM BP-1150 according to the BUDAPEST TREATY ON THE INTERNATIONAL RECOGNITION OF THE DEPOSIT OF MICROORGANISMS FOR THE PURPOSES OF PATENT PROCEDURE.

Step 2

Selection of *B. thuringiensis* subsp. aizawai IPL No. 7 by insecticidal activity test The clone of each of the 9 groups of purified *B. thuringiensis* subsp. aizawai IPL strain was grown on PY culture medium plates (15 cm in diameter) at 30 ° C. for 7 days. After the formation of spores and crystals of the insecticidal protein was confirmed with a phase contrast microscope, the cells were harvested and the freeze-thawing of the cells was repeated 3 times. The cells were suspended in 2 ml of distilled water and subjected to ultrasonification to give the crystals of the insecticidal protein in suspension.

A laboratory feed soaked with 1 ml of the suspension of the crystals, or its 10- or 100-fold dilution was given to a group of 10 cotton cutworm larvae (4th instar). After 3 days, the number of the dead insects was counted. The same test was conducted on larvae of diamond-back moth (3rd instar). When 1 ml of the suspension of the crystals of *B. thuringiensis* subsp. aizawai IPL No. 7 ($2.2 \times 10^7$ spores in 1 ml) was given to 10 larvae of diamond-back moth, all the 10 insects were dead. When 10 cotton cutworms were added to a suspension of the crystals ($2.6 \times 10^8$ spores in 1 ml), all the 10 were dead. Thus, the result proved that the *B. thuringiensis* subsp. aizawai IPL No. 7 produces a potent insecticidal activity against both of the noxious insects.

Cloning of gene coding for the insecticidal protein of *B. thuringiensis* aizawai IPL No. 7

Step 1

Synthesis of a DNA probe

A synthetic DNA probe (5'-CACAAATCCAG-CACCGGG-3') was designed in the light of the DNA sequence of the insecticidal protein gene of *Bacillus thuringiensis* subsp. kurstaki HD-1 Dipel [Whiteley et al., J. Biol. Chem. 260,6264–72 (1985)]. After the DNA oligomer was synthesized with a DNA synthesizer Model 380A (Applied Biosystems), 1 ml of 27% ammonium hydroxide was added to the DNA in a collecting vial and heated at 55° C. for 4 hours. The mixture was dried with a condensor. The dried DNA was dissolved in 100 μl of 0.01M triethyl-amine-acetic acid (TEAA)(pH 7.2), which was then applied to the reversed phase HPLC column C18 and eluted with a mixed solvent of acetonitrile-0.1M TEAA (pH 7.2). The fractions of an absorption peak at 260 nm were collected and dried. After addition of 100 μl of 80% acetic acid in acetonitrile, the mixture was allowed to stand for 15 minutes to turn to pale orange. The mixture was then dried up and combined with 100 μl of 0.01M TEAA (pH 7.2) and 100 μl of ethyl acetate. The ethyl acetate layer was removed off from the mixture, and 100 μl of diethyl ether was added instead. After the same procedures were repeated twice, the mixture was again dried up. The residues were dissolved in 0.01M TEAA (pH 7.2) and applied to HPLC. The fraction of the absorption peak at 260 nm was collected and dried. The residues were again dissolved in a mixture of 10 mM Tris-HCl (pH 7.5) and 1 mM EDTA (TE) solution. The thus prepared DNA probe was then labelled with $^{32}P$.

After 5 μl of the DNA probe prepared as above (about 100 p mole), 15 units of *E. coli* polynucleotide kinase (Takara Shuzo), 100 micro-Ci of [gamma$^{32}$-P]ATP (Amersham Japan) and 10 μl of 10-fold concentration of a reaction mixture [0.5 M Tris-HCl (pH 7.6), 0.1 M $MgCl_2$, and 0.1 M 2-mercaptoethanol] were combined, the mixture was made up to 100 μl with distilled water, and allowed to react at 37° C. for 1 hour. After the reaction mixture was admixed with a mixed solvent of chloroform and phenol (1:1), the supernatant was applied to a DE-52 column (Whatman)(0.5 ml bed size) equilibrated with TE buffer (pH 7.5). The column was washed with 3 ml of TE buffer (pH 7.5) and eluted with 0.7M NaCl-TE buffer (pH 7.5). The radioactive fractions were collected to give the $^{32}P$ labelled DNA probe.

Step 2

Preparation of the plasmid DNA library of *B. thuringiensis* subsp. aizawai IPL No. 7

*B thuringiensis* subsp. aizawai IPL No. 7 was grown in 200 ml of a PY liquid medium, and the harvested cells were washed with 30 ml of G buffer [10% glycerol, 1 mM EDTA and 50 mM Tris-HCl (pH 8.0)] and suspended in 8 ml of lysozyme (5 mg/ml). The mixture was allowed to react at 30° C. for 2 hours. After 16 ml of an alkaline solution [0.2 N NaOH and 1% sodium dodecyl sulfate (SDS)] was added thereto, the mixture was mixed gently and allowed to stand at room temperature for 10 minutes. Then, 12 ml of a neutralizing solution [3 M sodium acetate (pH 4.8)] was added to the mixture, and the mixture was allowed to stand at 4° C. for 1.5 hours. After centrifugation (14,000 rpm, 20 minutes), 70 ml of chilled ethanol was added to the supernatant, and the mixture was kept at −20° C. for 1 hour to precipitate DNA. The DNA was collected, dried up and suspended in 5 ml of 0.1 M sodium acetate. The suspension was treated twice with phenol equilibrated with TE buffer (pH 7.5). After the supernatant was collected, 2 volumes of chilled ethanol was added to it to precipitate DNA. The dried DNA was resuspended in 6 ml of TE buffer (pH 7.5) and the plasmid DNA was purified by CsCl equilibrium density gradient centrifugation. The plasmid DNA (5 μg) was digested with 10 units of restriction enzyme Bam HI. The same volume of a mixed solvent of phenol and chloroform (1:1) was added to the mixture to yield a supernatant. Ethanol was added to the supernatant to precipitate DNA. The DNA was dried up and suspended in 20 μl of TE buffer (pH 7.5).

On the other hand, 2 μg of a pUC 8 vector plasmid (Pharmacia) was digested with 5 units of a restriction enzyme, Bam HI, and a DNA was recovered by same procedures as above, and suspended in 20 μl of TE buffer (pH 7.5). To this suspension, 5 μl of *E. coli* alkaline phosphatase (Takara Shuzo, 2.0 units), 50 μl of 0.1 M Tris-HCl buffer (pH 8.0) and 15 μl of distilled water were added, and incubated at 60° C. for 1 hour. The DNA was recovered by treating the reaction mixture twice with phenol-chloroform and precipitating the DNA from the isolated supernatant with ethanol, and suspended in 20 μl of TE buffer (pH 7.5).

To a mixture of 15 μl of the plasmid DNA Bam HI fragments and 15 μl of the Bam HI fragments of the pUC 8 vector DNA, were added 1 μl of T4 DNA ligase (Takara Shuzo,0.1 unit), 7.5 μl of 0.1 M dithiothreitol (Nakarai Chemical), 7.5 μl of 10 mM adenosine triphosphate (Nakarai Chemical), 25 μl of a 3-fold concentration reaction mixture [200 mM Tris-HCl (pH 7.6) and 20 mM $MgCl_2$] and 5 μl of distilled water until the mixture had the total volume of 75 μl. The mixture was then incubated at 14° C. for 6 hours. The resulting ligase reaction mixture (10 μl) was added 100 μl of suspension of competent cells of *E. coli* DHl (ATCC 33849), which had been prepared by the method of Scott et al., Cell Technology, 2, 616–626, (1983)]. The mixture was incubated at 0° C. for 15 minutes and heated at 42° C. for 40 seconds. After 0.9 ml of an L broth liquid medium [tryptone 10 g, yeast extract 5 g, NaCl 5 g, glucose (Nakarai Chemical) 1 g and distilled water equal to 1 liter] was added, the cells were incubated at 37° C. for 1 hour and grown on an L broth plate medium (1.2% agar in the L broth liquid medium) containing a final concentration of 50 μg/ml of ampicillin.

Step 3

Isolation of a clone carrying the insecticidal protein gene by colony hybridization The colonies spread on a plate were replicated on 2 nitrocellulose filters, which were then placed on a plate culture medium containing ampicillin (50 μg/ml) and chloramphenicol (600 μg/ml) and incubated overnight. Each of the filter was treated with 2.5 ml/filter of 0.5 N NaOH for 5 minutes and air-dried. The same volume of 1 M Tris-HCl (pH 7.5) was added to the filter and allowed to stand for 5 minutes. After being air-dried, the filter was treated with 2.5 ml of 1 M Tris-HCl (pH 7.5)1.5 M NaCl for 5 minutes, air-dried and treated at 80 ° C. for 3 hours under vacuum. After addition of 10 ml/4 filters of 0.1% SDS-4×SSC [SSC: 0.15 M NaCl - 0.015 M sodium citrate (pH 7.5)], the filters were treated at 60° C. for 15 minutes. The colonies on the filters were wiped off and the filters were immersed in 6 ml of prehybridization solution [4×SSC, 10×Denhart, 100 μg/ml salmon testis single stranded DNA (Sigma); wherein 10×Denhart is a solution containing 0.2% ficoll, 0.2% polyvinylpyrrolidone and 0.2% BSA) and treated at 60 ° C. for 3 hours. The $^{32}P$ labeled synthetic DNA probe prepared in Step 1 was added to the prehybridization solution, and the filters were placed in the mixture and incubated at 56° C. overnight. After hybridization, the filters were washed with 4×SSC×-0.1% SDS solution at 56° C. for 15 minutes for 4 times and dried. The filters were placed on X-ray films to conduct radioautography. The positive colonies were collected from the master plate and the colony hybridization of the colonies was performed in the same manner as above to isolate a positive clone which was named as *E. coli* DH1/pAB6.

Analysis of the insecticidal protein gene of *B. thuringiensis* subsp. aizawai IPL No. 7

The plasmid pAB6 was isolated from the thus isolated positive clone *E. coli* DH1/pAB6 according to the method of Birnboim and Doly. The restriction map (FIG. 3, upper part) of the insert DNA (22.4 kb) was prepared by digesting the plasmid pAB6 with various restriction enzymes including Bam HI, Hind III, Pst I, Bgl II, Pvu II, Eco RI, Aha III, Kpn I and Cla I, and analyzed by 0.7% agarose gel electrophoresis. By using the synthetic DNA probe prepared as above, Southern hybridization [J. Mol. Biol., 98 503-517 (1975)] was carried out to identify the region coding for the insecticidal protein gene in the insert DNA, and the detailed restriction map of the region was prepared (FIG. 3 lower part).

After DNA fragments obtained by digesting the DNA were sub-cloned in vector pUC8, the plasmid DNAs containing these DNA fragments were isolated by the method of Birnboim and Doly. Each of the isolated DNAs was suspended in 18 μl of TE buffer (pH 7.5) and 2 μl of 2 N NaOH was added to the suspension, which was then allowed to stand at room temperature for 5 minutes. Following the addition of 8 μl of 7.5 M ammonium acetate, 100 μl of chilled ethanol was added to the mixture to precipitate DNA. The DNA was recovered by centrifugation (12,000 rpm, 5 minutes), dried and dissolved in distilled water in a concentration of 0.5 pmole/5 ml. After 1.5 μl of 10-fold concentration of Klenow-buffer (Takara Shuzo), 1 μl of primer DNA (P-L Biochemicals) and 4.5 μl of distilled water was added to 5 μl of the plasmid DNA(5 pmole) prepared as above, to make the total volume 12 μl, the mixture was heated at 60 ° C. for 15 minutes and allowed to stand at room temperature for 20 minutes The reaction mixture was mixed with 2 μl of [alpha- $^{32}P$] ATP (400 Ci/mmole, Amersham Japan) and 1 μl of Klenow fragment enzyme (Takara Shuzo, 2 units).

The mixture (3.2 μl) was added to 4 kinds of dNTP+ddNTP mixture (Takara Shuzo, 2 μl each) and allowed to stand at 42° C. for 20 minutes. After 1 μl of a Chasesolution (Takara Shuzo) was added to each of the resulting mixtures, the mixtures were allowed to stand at 42° C. for 20 minutes. After addition of 6 μl of 95% formamide staining solution (0.1% bromophenol and 0.1% xylenecyanol), the mixtures (2 μl) were applied to 6% acrylamide-urea gel, which was prepared by a conventional method, and electrophoresis at 1700 V for 6 hours. The gel was dried and placed on X-ray films. After the films were processed, the DNA sequences were determined.

The DNA sequence of the insecticidal protein gene of *B. thuringiensis* subsp. aizawai IPL No. 7 is given in FIG. 2. As shown in FIG. 2, the gene has 3465 bp of coding region starting from ATG and ending at the stop codon TAA and encodes 1155 amino acids.

1. Construction of expression plasmids pAH8 and pAH7 for expression of the insecticidal gene of *B. thuringiensis* subsp. aizawai IPL No. 7 in *E. coli* cells Step 1

Preparation of DNA Aha III fragment

Approximately 10 μg of the recombinant plasmid pAB6 carrying the insecticidal protein gene was allowed to react with ca. 30 units of restriction enzyme Aha III at 37° C. for 1 hour in 30 μl of Aha III reaction solution [10 mM Tris-HCl (pH 7.5), 60 mM NaCl, 7 mM $MgCl_2$, 10 mM EDTA and 1 mM dithiothreitol]. The reaction mixture was subjected to gel electrophoresis on 0.8% low melting point agarose gel (Bethesda Research Laboratory) containing 0.1 μg/ml of ethidium bromide. The portion of the gel containing 3.5 kb of the DNA Aha III fragment was isolated under ultraviolet rays, placed in a test tube and heated at 65° C. for 5 minutes. TE buffer [10 mM Tris-HCl (pH 8.0), 0.5 mM EDTA] (2 times the volume of the used gel) was added into the tube and the mixture was extracted with phenol saturated with TE buffer. After centrifugation at 10,000 rpm for 5 minutes, the upper layer was combined with 1/40 volume of 4 M NaCl and 2 volumes of ethanol, and allowed to stand at −80° C. for 10 minutes to precipitate DNA. The DNA was collected by centrifugation at 10,000 rpm for 10 minutes and suspended in 10 μl of distilled water.

Step 2

Preparation of a vector

Expression vector pUC 18 (Pharmacia) 1 μg was digested with 1 unit of a restriction enzyme, Hinc II (Takara Shuzo) at 37° C. for 1 hour in 20 μl of Hinc II reaction solution [10 mM Tris-HCl (pH 7.4), 100 mM NaCl, 7 mM $MgCl_2$ and 10 mM dithiothreitol]. The same volume of a mixed solvent of phenol-chloroform (1:1) was added to the reaction mixture. After being stirred, the mixture was centrifugated at 10,000 rpm for 5 minutes to yield a supernatant, to which 2 volumes of chilled ethanol was added. The mixture was then kept at −80° C. for 15 minutes and centrifugated at 10,000 rpm for 10 minutes. The precipitated DNA was collected and suspended in 10 μl of distilled water.

Step 3

Construction of expression plasmids pAH7 and pAH8

The DNA Aha III fragment obtained in step 1 and the expression vector pUC 18 prepared in Step 2, 1 μg each, were mixed and reacted with 7.2 units of T4 DNA ligase (Takara Shuzo) at 16° C. for 2 hours in 45 μl of a ligase reaction solution [66 mM Tris-HCl (pH 7.6), 6.6 $MgCl_2$, 10 mM dithiothreitol and 1.0 mM ATP]. With this reaction mixture, *E. coli* JM103 (Pharmacia) was transformed in accordance with the method of Cohen et al. [Proc. Natl. Acad. Sci. USA., 69. 2110-2114 (1972)]. The ampicillin resistant colonies were cultured and the plasmid DNA was isolated according to the method of Birnboim et al.

Approximately 1 μg of the plasmid DNA was digested with 3 units of restriction enzyme, Hind III, at 37° C. for 1 hour in a Hind III reaction solution [10 mM Tris-HCl (pH 7.5), 60 mM NaCl, 10 mM $MgCl_2$, 1 mM 2-mercaptoethanol and 100 μg/ml bovine serum albumin] and analyzed on agarose gel electrophoresis. The expression plasmid in which the insecticidal protein gene is ligased in the same direction as the lac promoter of the vector was named as pAH8. The expression plasmid in which the gene is ligased in the opposite direction was named as pAH7 (See FIG. 1).

2. Construction of expression plasmid pTBl for use in expression of the insecticidal protein gene of *B. thuringiensis* subsp. aizawai No. 7 in *E. coli* cells Step 1

Preparation of Pst I - Bam HI fragment containing the insecticidal protein gene

Approximately 5 μg of the expression plasmid pAH8 containing the insecticidal protein gene was digested with about 20 units of a restriction enzyme, Pst I, and about 20 units of restriction enzyme, Bam HI, at 37° C. for 1 hour in 50 μl of a Pst I reaction solution [10 mM Tris-HCl (pH 7.5), 50 mM NaCl, 10 mM MgCl$_2$, 1 mM 2-mercaptoethanol and 100 μg/ml bovine serum albumin]. The reaction mixture was mixed with 30 μl of phenol saturated with TE buffer for phenol extraction. The mixture was centrifugated at 10,000 rpm for 5 minutes and the upper layer was collected. After addition of 1/40 volume of 4 M NaCl and 2 volumes of ethanol, the layer was allowed to stand at −80° C. for 10 minutes and then centrifugated at 10,000 rpm for 10 minutes to recover DNA. The recovered DNA was dried and suspended in 20 μl of distilled water.

Step 2

Construction of a vector

Approximately 5 μg of expression vector pKK223-3 (Pharmacia) was digested with 0.1 unit of a restriction enzyme, Bam HI, (Takara Shuzo) at 37° C. for 15 minutes in a Bam HI reaction solution [10 mM TrisHCl (pH 8.0), 7 mM MgCl$_2$, 100 mM NaCl, 2 mM 2-mercaptoethanol and 0.01% bovine serum albumin]. The reaction mixture was supplied to 0.8% low melting point agarose gel containing 0.1 μg/ml of ethidium bromide. The portion of the gel wherein the vector DNA (4.6 kb) resulting from the cleavage at one of the two Bam HI sites of the vector pKK 223-3 was possibly contained was isolated under ultraviolet rays, placed in a test tube and heated at 65° C. for 5 minutes to melt the gel. The DNA was recovered from the gel by phenol extraction and ethanol precipitation, and suspended in 20 μl of distilled water.

To this DNA suspension, a final concentration of 3 mM of 4 kinds of deoxynucleotides and 5 units of *E. coli* DNA polymerase I large fragment were added, and the mixture was reacted at 25° C. for 2 hours in 60 μl of a Hind III reaction solution [10 mM Tris-HCl (pH 7.5), 60 mM NaCl, 10 mM MgCl$_2$, 1 mM 2-mercaptoethanol and 100 μg/ml bovine serum albumin]. DNA was recovered by phenol extraction and ethanol precipitation, and suspended in 20 μl of distilled water. Approximately 1 μg of the DNA obtained as above was allowed to react with 3 units of T4 DNA ligase at 16° C. for 2 hours in 45 μl of a ligase reaction solution [66 mM Tris-HCl (pH 7.6), 6.6 mM MgCl$_2$, 10 nM dithiothreitol and 1.0 nM ATP]. With the reaction mixture, *E. coli* JM103 cells were transformed in accordance with the method of Cohen et al. The colonies resistant to ampicillin were grown and the plasmid DNA was isolated from the transformants according to the method of Birnboim et al. Approximately 1 μg of the plasmid DNA was digested with 3 units of restriction enzyme Bam HI at 37° C. for 1 hour in a Bam HI reaction solution and the reaction mixture was subjected to the agarose gel electrophoresis analysis. By analysis of the plasmid DNA, the plasmid wherein the Bam HI site in the multicloning sites of the pKK223-3 plasmid was retained, but the other Bam HI site was vanished, was selected and named as pKK223-4.

Approximately 5 μg of the pKK223-4 DNA was digested with 10 units of restriction enzyme Pst I and 10 units of restriction enzyme Bam HI at 37° C. for 1 hour in 50 μl of a Pst I reaction solution [10 mM Tris-HCl(pH 7.5), 50 mM NaCl, 10 mM MgCl$_2$, 1 mM 2-mercaptoethanol and 100 μg/ml of bovine serum albumin]. DNA was recovered by phenol extraction and ethanol precipitation, and suspended in 20 μl of distilled water.

Step 3

Construction of expression plasmid pTBl

The Pst I - Bam HI DNA fragment obtained in Step 1 and the vector pKK223-4 obtained in Step 2, 1 μg each, were combined and the mixture was allowed to react with 7.2 units of T4 DNA ligase (Takara Shuzo) at 16° C. for 2 hours in 45 μl of a ligase reaction solution [66 mM Tris-HCl (pH 7.6), 6.6 mM MgCl$_2$, 10 mM dithiothreitol and 10 mM ATP]. With the reaction mixture, *E. coli* JM103 was transformed according to the method of Cohen et al.

Figure 1:
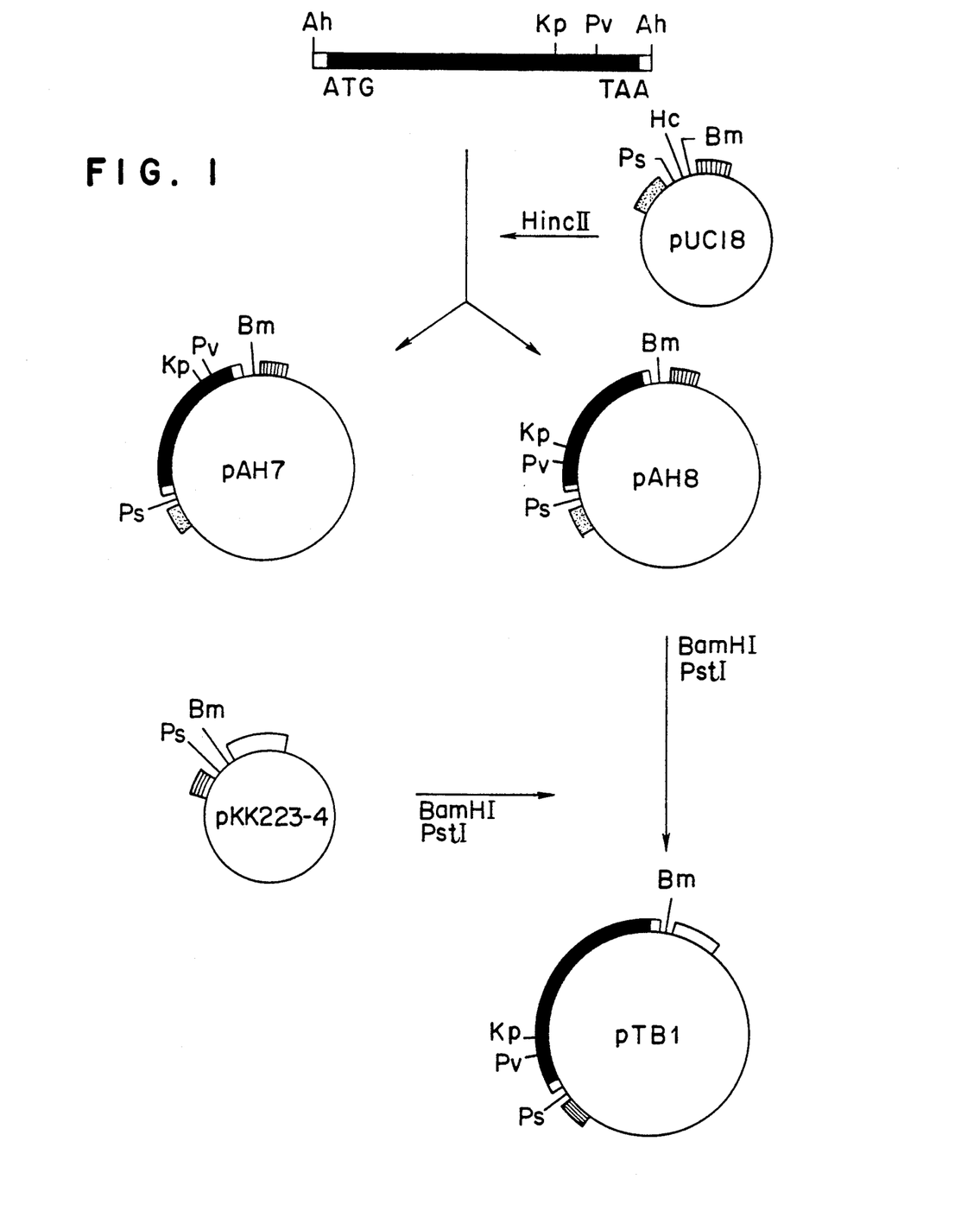
FIG. 1 is a diagram of the construction of the expression plasmids pAH7, pAH8 and pTB1. Black boxes indicate the gene coding for the insecticidal protein, boxes with vertical lines lac promoter, boxes with horizontal lines ribosome RNA terminator, white boxes tac promoter and dotted boxes lacZ gene. ATG and TAA indicate the initiation codon and stop codon of the insecticidal protein gene, respectively. Ah, Kp, Pv, Bm, Hc and Ps indicate restriction enzymes Aha III, Kpn I, Pvu II, Bam HI, Hinc II and Pst I, respectively.

The colonies resistant to ampicillin were grown and the plasmid DNA was isolated. Approximately 1 μg of the plasmid DNA was digested with 3 units of a restriction enzyme, Bam HI, at 37° C. for 1 hour in 30 μl of a Bam HI reaction solution and the reaction mixture was subjected to agarose gel electrophoresis analysis. The plasmid wherein the insecticidal protein gene was inserted downstream of the tac promoter of the expression vector was selected and named as expression plasmid pTBl (See FIG. 1).

3. Production of the insecticidal protein in *E. coli*

In accordance with the method of Cohen et al., *E. coli* JM103 cells were transformed with each of the expression plasmids pAH7, pAH8 and pTBl.

The analysis of the insecticidal protein of *B. thuringiensis* subsp. aizawai IPL produced by the resulting transformant *E. coli* JM103/pAH7, JM103/pAH8 and JM103/pTBl was carried out as follows:

Each of the transformants was grown overnight in an L broth liquid medium [tryptone (Difco) 10 g, NaCl 5 g, yeast extract (Difco) 5 g and distilled water equal to 1 liter]. The resulting culture medium, 0.1 ml, was inoculated to 10 ml of an L broth liquid medium and cultured at 37 ° C. When the OD 660 nm was reached to 0.1, a final concentration of 2 mM of isopropylthiogalactoside was added to the medium. After being cultivated at 37° C. for 20 hours, 0.3 ml of the culture medium was centrifugated (3,000 rpm, 15 minutes) to harvest the cells. The cells were suspended in 50 μl of a sample buffer [62.5 mM Tris-HCl (pH 8.0), 2% (w/w) sodium dodecyl sulfate, 5% (v/v) 2-mercaptoethanol, 10% (w/v) glycerol and 0.01% bromophenol blue]. After being heated at 100° C. for 5 minutes, the suspension was applied to SDS-polyacrylamide gel electrophoresis according to the method of Laemmli [Nature 227, 680–685 (1970)]. The gel was stained with coomassie brilliant blue, destained, dried and fixed on a filter paper. A band of the insecticidal protein of molecular weight of 125 K daltons, which was allowed to cross-react with anti-insecticidal protein antibody (IgG), was observed with the gels of the transformant *E. coli* JM103 cells containing the expression plasmids.

Figure 4:
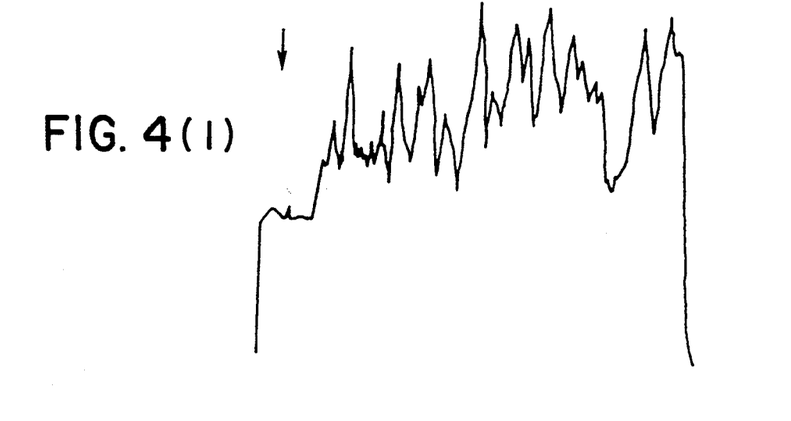
FIG. 4 shows the results of the quantitative analysis of the insecticidal protein produced by the transformant *E. coli* with a densitometer. (1), (2) and (3) are the results of the measurements of the insecticidal proteins in the crude extract of transformant *E. coli* JM103/pAH7, JM103/pAH8 and JM103/pTB1, respectively. The arrows indicate the peaks of the bands of the insecticidal protein.

The measurement of the protein bands on the gels with a densitometer indicated that *E. coli* JM103/pAH7, JM103/pAH8 and JM103/pTBl produced the insecticidal protein in amounts of 1%, 8% and 35% of the total protein, respectively (See FIG. 4). Thus, it was confirmed that these transformants of *E. coli* effectively produced the insecticidal protein of *B. thuringiensis* aizawai IPL.

4. Isolation of the insecticidal protein produced in the transformant *E. coli* cells The transformant E. coli cells were grown overnight in an L broth liquid medium, and 0.1 ml of the culture medium was inoculated to 10 ml of an L broth medium. The culture was incubated at 37° C. until the OD 660 nm value reached to 0.1, when a final concentration of 2 mM of isopropylthiogalactoside was added to the medium. After being further cultivated, 5 ml of the culture medium was centrifugated at 3,000 rpm for 15 minutes to harvest the cells. The cells were frozen at −80° C. and thawed at room temperature. This freeze-thawed procedure was repeated 3 times. The cells were suspended in 2 ml of TE buffer [10 mM Tris-HCl (pH 7.5) and 1 mM EDTA] and ultrasonificated for 30 seconds for 3 times.

The resulting crude extract was centrifugated at 7,000 rpm for 10 minutes to yield precipitates. The precipitates were resuspended in the sample buffer for electrophoresis and analyzed on SDS-PAGE to find that about 80% of the total protein of the precipitates was the insecticidal protein. Thus it was confirmed that the insecticidal protein can effectively be isolated by the procedures described above. It was also confirmed that these procedures can be applied to a large volume culturing.

We claim:

1. A plasmid carrying a DNA sequence coding for the insecticidal protein of Bacillus thuringiensis subsp. aizawai IPL given in FIG. 2.

2. A plasmid according to claim 1, which is named as pAB6.

3. A recombiant expression vector carrying a DNA sequence coding for the insecticidal protein of Bacillus thuringiensis subsp. aizawai IPL given in FIG. 2, and being capable of producing said insecticidal protein in host cells.

4. A recombinant expression vector according to claim 3, wherein the DNA sequence is as given in FIG. 2.

5. A recombinant vector according to claim 3, which is selected from the group consisting of pAH8, pAH7 and pTB1.

6. A microorganism carrying a recombinant plasmid containing a DNA sequence coding for the insecticidal protein of Bacillus thuringiensis subsp. aizawai IPL given in FIG. 2.

7. A microorganism according to claim 6, which belongs to E. coli.

8. A microorganism according to claim 6, wherein the recombinant plasmid is pAB6, pAH8, pAH7 or pTB1.

Figure 2:
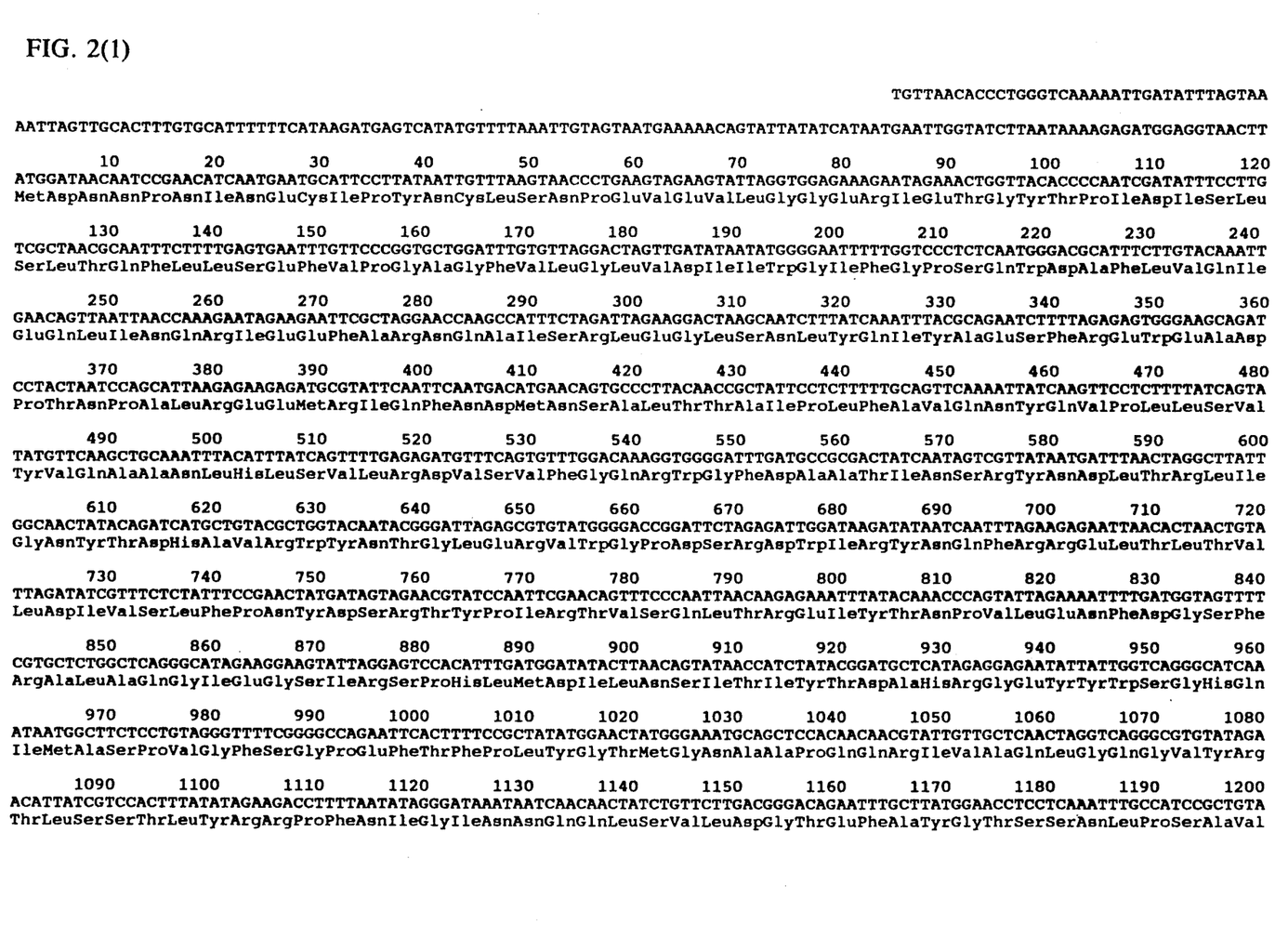
Figure 3:
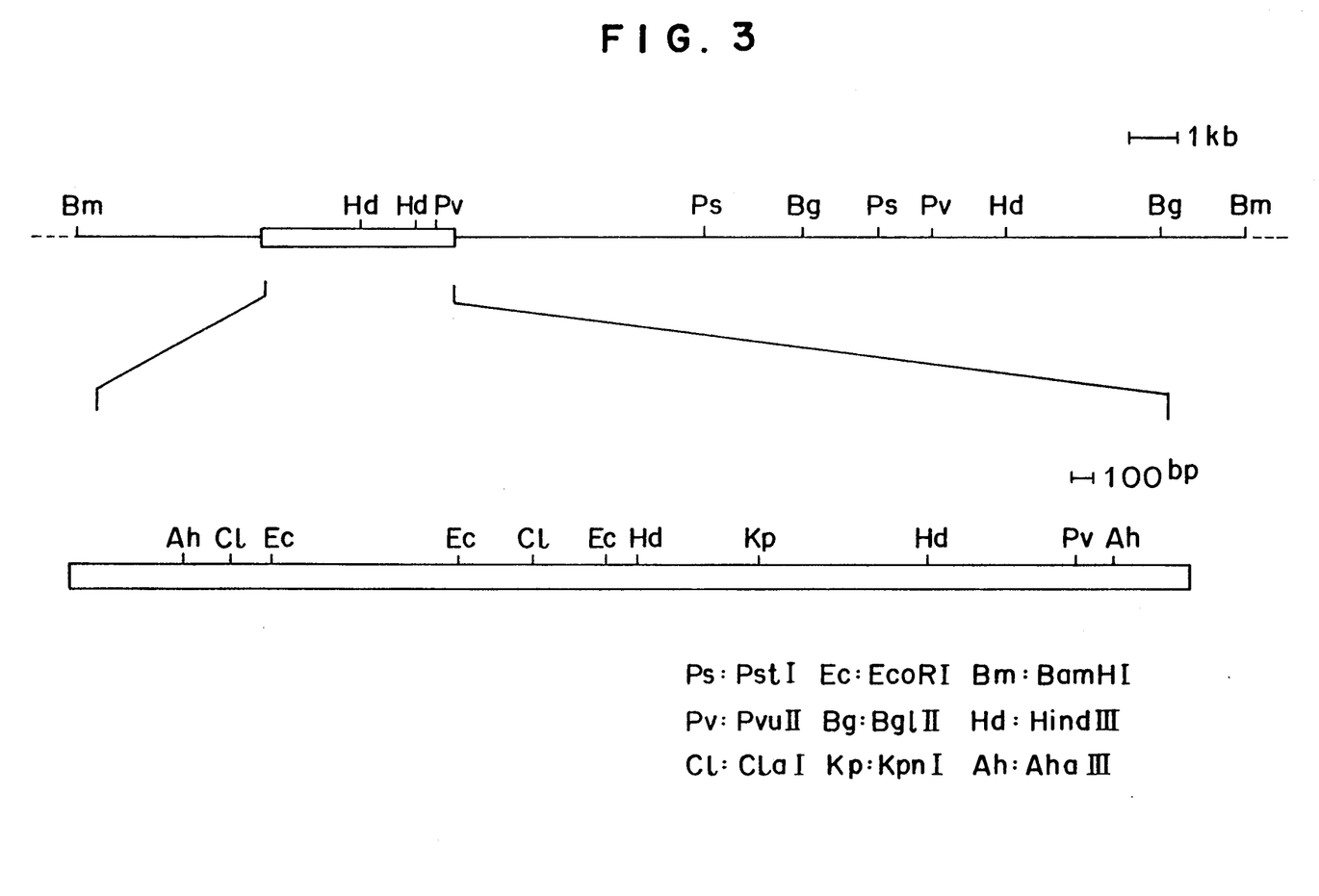
FIG. 3 is a restriction map of the insert DNA [22.4 Kilo base(kb)] of the plasmid pAB6. The insecticidal protein gene of *B. thuringiensis* subsp. aizawai IPL is indicated by open boxes. A detailed restriction map of the gene is given in the lower box.

9. A process for producing the insecticidal protein of Bacillus thuringiensis subsp. aizawai IPL which comprises:

culturing a microorganism carrying a recombinant expression vector harboring a gene coding for the protein described in FIG. 2 in a suitable medium; and collecting the produced protein.

10. A plasmid which is pTB1.

11. A microorganism carrying a recombinant plasmid, wherein said microorganism belongs to E. coli, and wherein said recombinant plasmid is pTB1.

12. A microorganism which is E. coli JM103/pTB1.

13. A DNA encoding for the insecticidal protein of FIG. 2.

14. The DNA of claim 13 comprising a DNA sequence wherein said DNA sequence is that of FIG. 2.

15. A DNA sequence as given in FIG. 2, coding for the insecticidal protein of Bacillus thuringiensis sub-species aizawai IPL having the amino acid sequence given in FIG. 2.

* * * * *